United States Patent
Ripplinger

(10) Patent No.: US 11,648,050 B2
(45) Date of Patent: May 16, 2023

(54) INSTRUMENT FOR THE COAGULATION AND DISSECTION OF BIOLOGICAL TISSUE AND METHOD FOR OPERATING SUCH AN INSTRUMENT

(71) Applicant: Erbe Elektromedizin GmbH, Tuebingen (DE)

(72) Inventor: Thomas Ripplinger, Tuebingen (DE)

(73) Assignee: ERBE ELEKTROMEDIZIN GMBH, Tuebingen (DE)

( * ) Notice: Subject to any disclaimer, the term of this patent is extended or adjusted under 35 U.S.C. 154(b) by 648 days.

(21) Appl. No.: 16/653,067

(22) Filed: Oct. 15, 2019

(65) Prior Publication Data
US 2020/0113623 A1 Apr. 16, 2020

(30) Foreign Application Priority Data
Oct. 16, 2018 (EP) .................................... 18200797

(51) Int. Cl.
A61B 18/14 (2006.01)
H03K 17/687 (2006.01)
A61B 18/00 (2006.01)

(52) U.S. Cl.
CPC ....... *A61B 18/1445* (2013.01); *H03K 17/687* (2013.01); *A61B 2018/0094* (2013.01);
(Continued)

(58) Field of Classification Search
CPC ........... A61B 2018/00708; A61B 2018/00958; A61B 2018/1246; A61B 2018/00922;
(Continued)

(56) References Cited

U.S. PATENT DOCUMENTS 3,628,087 A * 12/1971 Wigert .................. H02M 3/137
315/225
3,681,574 A * 8/1972 Caulkin .............. H04M 1/2725
377/55
(Continued)

FOREIGN PATENT DOCUMENTS

CN 101677834 A 3/2010
CN 105395248 A 3/2016
(Continued)

OTHER PUBLICATIONS

European Search Report dated Apr. 26, 2019, in corresponding European Application No. 18200797.1 (9 pages).
(Continued)

*Primary Examiner* — Oommen Jacob
(74) *Attorney, Agent, or Firm* — Fitch, Even, Tabin & Flannery LLP

(57) ABSTRACT

An instrument for coagulation and dissection of biological tissue including a tool with coagulation electrodes and at least one cutting electrode. The electrodes are actuated via an operating circuit including an evaluation circuit, to which an external apparatus delivers an evaluation signal with first and second half-waves having opposite polarities. During at least one first half-wave, the evaluation circuit checks whether a first switch or a second switch are actuated on the instrument. Depending on the evaluation result, a triggering signal is transmitted to a switching unit. Depending on the triggering signal, the switching unit is switched into a first or second switching state. In the second switching state, no voltage suitable for dissection and no current suitable for dissection, respectively, is applied to the cutting electrode. In the first switching state, a voltage suitable for dissection or a current suitable for dissection is applied to the cutting electrode.

16 Claims, 7 Drawing Sheets

(52) U.S. Cl.
CPC ........... *A61B 2018/00607* (2013.01); *A61B 2018/00827* (2013.01); *A61B 2018/00892* (2013.01); *A61B 2018/00922* (2013.01); *A61B 2018/00928* (2013.01); *A61B 2018/00934* (2013.01)

(58) Field of Classification Search
CPC ...... A61B 2018/00607; A61B 18/1445; A61B 2018/00928; A61B 2018/00934; A61B 2018/0094; H03K 17/687
See application file for complete search history.

(56) References Cited

U.S. PATENT DOCUMENTS

| | | | | |
|---|---|---|---|---|
| 3,772,684 | A | * | 11/1973 | Scantlin ............ H04L 25/40 336/131 |
| 4,187,670 | A | * | 2/1980 | Okano ............ G04G 13/00 968/968 |
| 5,523,633 | A | * | 6/1996 | Imaizumi ............ H01H 1/605 307/137 |
| 5,675,227 | A | * | 10/1997 | Roos ............ H01H 7/00 318/446 |
| 5,854,448 | A | * | 12/1998 | Nozaki ............ G06F 3/041 178/18.05 |
| 6,022,347 | A | | 2/2000 | Lindenmeier et al. |
| 6,197,026 | B1 | | 3/2001 | Farin et al. |
| 6,909,313 | B2 | * | 6/2005 | Youssef ............ H03K 17/18 327/147 |
| 7,215,257 | B2 | * | 5/2007 | Ota ............ H03K 5/1254 341/26 |
| 8,130,022 | B2 | * | 3/2012 | Tyrrell ............ H03K 5/1254 327/518 |
| 2004/0172015 | A1 | | 9/2004 | Novak |
| 2011/0196398 | A1 | | 8/2011 | Robertson et al. |
| 2011/0249471 | A1 | * | 10/2011 | Costa ............ H02J 9/005 363/13 |
| 2013/0120306 | A1 | * | 5/2013 | Furukawa ............ G06F 3/041 345/173 |
| 2013/0307550 | A1 | * | 11/2013 | Densham ............ H02J 7/0048 324/426 |
| 2014/0005680 | A1 | | 1/2014 | Shelton, IV et al. |
| 2014/0018795 | A1 | * | 1/2014 | Shilev ............ A61B 18/1402 606/41 |
| 2017/0049505 | A1 | * | 2/2017 | Weiler ............ A61B 18/1445 |
| 2020/0113623 | A1 | * | 4/2020 | Ripplinger ......... A61B 18/1233 |

FOREIGN PATENT DOCUMENTS

| | | |
|---|---|---|
| CN | 106562821 A | 4/2017 |
| CN | 106803722 A | 6/2017 |
| DE | 4332614 A1 | 3/1994 |
| DE | 102010025298 A1 | 12/2011 |
| EP | 0832612 A1 | 4/1998 |
| EP | 3132765 A1 | 2/2017 |
| JP | 2013078585 A | 5/2013 |
| JP | 2013519436 A | 5/2013 |
| JP | 2013529992 A | 7/2013 |
| RU | 2015102586 A | 8/2016 |
| WO | 02/100283 A1 | 12/2002 |

OTHER PUBLICATIONS

Indian Patent Office, Examination Report for Application No. 201914041245 dated Sep. 6, 2022; 6 pages.
Chinese Patent Office, Office Action and Search Report for Application No. 201910984127.4, with machine English translation dated Aug. 17, 2022; 12 pages.
Russian Patent Office, Grant Decision dated Feb. 1, 2023 for RU2019131839; 11 pages.
Japanese Patent Office; Notice of Reasons for Refusal; Japanese Patent Application No. 2019-187411, dated Feb. 22, 2023; 7 pages.

* cited by examiner

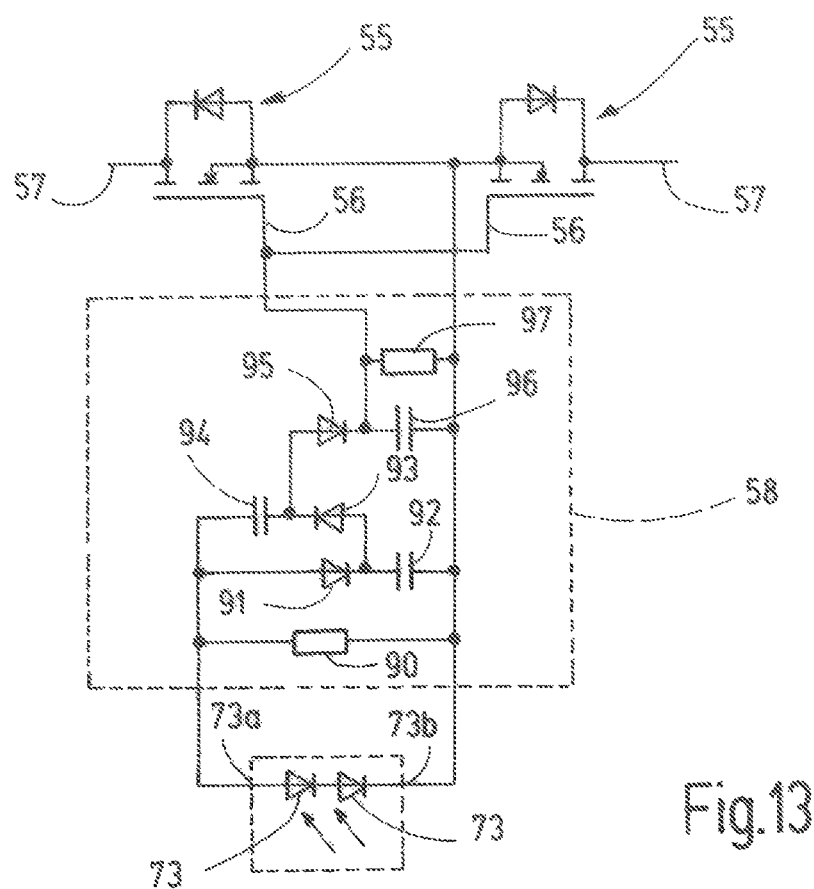
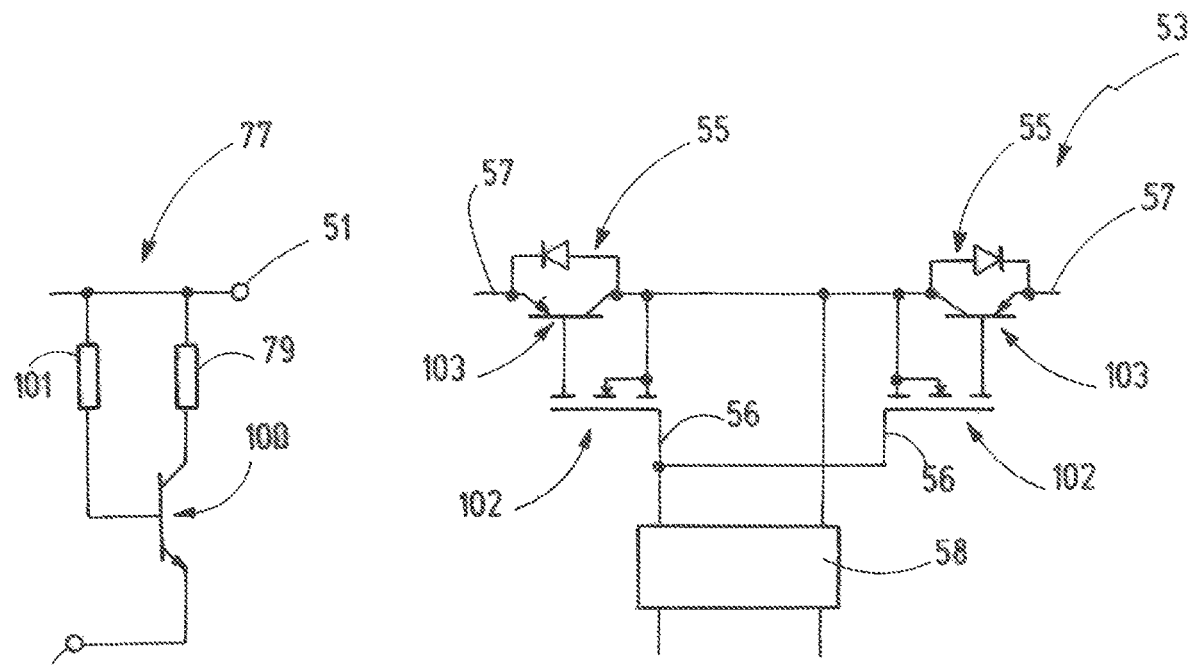
Fig.13
Fig.14
Fig.15

INSTRUMENT FOR THE COAGULATION AND DISSECTION OF BIOLOGICAL TISSUE AND METHOD FOR OPERATING SUCH AN INSTRUMENT

RELATED APPLICATION(S)

This application claims the benefit of European Patent Application No. 18200797.1, filed Oct. 16, 2018, the contents of which are incorporated herein by reference as if fully rewritten herein.

TECHNICAL FIELD

The invention relates to an instrument for the coagulation and dissection of biological tissue.

BACKGROUND

Such an instrument has been known from publication EP 3 132 765 A1, for example. The instrument comprises a tool with a cutting electrode and several coagulation electrodes. By means of an operating circuit, it is possible to supply the electrodes with electrical energy. To accomplish this, the operating circuit comprises a transformer which is connected—on its secondary side—to a power switch via a cable, for example. The instrument comprises a cutting actuation switch and a coagulation actuation switch. The coagulation actuation switch is mechanically coupled with the power switch. When the coagulation activation switch is actuated, the electrical connection between the cutting electrode and the transformer is disconnected or reversed, so that no cutting voltage is applied to the cutting electrode.

Instruments for the coagulation and/or the dissection of biological tissue are offered as multiple use instruments and also as single use instruments. In particular in the case of single use instruments, manufacturing costs play a large part. Therefore, the object of the present invention can be viewed as providing an instrument that is simple and safe to operate and that can be manufactured in a cost-effective manner.

SUMMARY

This object is achieved with instruments and methods as disclosed herein.

The instrument is adapted for the coagulation and dissection of biological tissue. It comprises a tool with at least one cutting electrode and at least one coagulation electrode pair. Each coagulation electrode pair includes a first coagulation electrode and a second coagulation electrode. The instrument comprises an operating circuit. The operating circuit has a cutting output connected to the cutting electrode, a first coagulation output connected to the at least one coagulation electrode, and a second coagulation output connected to the at least one second coagulation electrode. Furthermore, the operating circuit comprises a supply connection by means of which a supply voltage or a supply current is provided. Furthermore, there is an evaluation connection, by means of which a period evaluation signal including first half-waves having one polarity and second half-waves having respectively the other polarity. For example, the first half-waves are negative half-waves, and the second half-waves are positive half-waves of the evaluation signal. The evaluation signal may be a current or a voltage.

Additionally, the operating circuit has an evaluation connection comprising a manually actuatable first switch and a triggering element for generating a triggering signal. The triggering element may be a single component or a group of several individual components. The evaluation circuit is adapted to evaluate, during at least one of the first half-waves, whether or not the first switch was actuated. Depending on this evaluation result, starting with one of the subsequent second half-waves the triggering signal will be generated corresponding to the evaluation result. By means of the triggering signal, a controllable switching unit is switched between a first switching state and a second switching state. The switching unit may be directly or indirectly connected to the supply input and the cutting input, respectively. In a preferred embodiment, said switching unit may be arranged in series between the supply connection and the cutting output. In this case, the switching unit may be switched, for example, between a conducting and a blocking switching state. It is also possible to switch the switching unit between two conducting switching states, wherein the cutting output is supplied with different voltages or currents. In the first switching state of the switching unit, an electrical voltage is applied to the cutting output and hence the cutting electrode or an electrical current is provided, said current being suitable for the dissection of biological tissue. As opposed to this, in the second switching state, there is no electrical voltage or electrical current sufficient for the dissection of biological tissue available on the cutting electrode. In the second switching state, there may either be essentially no voltage or no current available on the cutting electrode or, alternatively, there may be provided a voltage or a current that is not suitable for the dissection but is suitable, for example, for the coagulation.

The evaluation signal for the query whether or not the first switch was actuated is provided by an apparatus to which the instrument can be connected. The actuation state of the first switch is evaluated during at least one first half-wave and, in the event of a change of the actuation state, the triggering signal is adapted to the changed actuation state of the first switch during at least one of the subsequent second half-waves. Furthermore, the apparatus can provide the instrument on the supply input with a supply voltage or a supply current, when the actuation of the first switch has been detected. In particular, the switching unit is switched—with the first switch not actuated by the triggering signal—into the second switching state, in which no electrical energy is available for the dissection on the cutting electrode. If the actuation of the first switch is detected, a triggering signal is generated, said signal switching the switching unit into the first switching state, in which then an electrical energy for dissection is made available on the cutting electrode.

A mechanical coupling between the switching unit and the evaluation circuit may be omitted. The instrument may be constricted in an extremely simple manner with standard components. In particular, it is possible to structure the switching unit via one or more semiconductor switches. Mechanical switches in the switching unit may be omitted. As a result, a simple avoidance of spark or arc formation during the change of the switching state is achieved. It is also possible to implement the solution in a cost-effective manner in single use instruments.

It is advantageous if the operating circuit comprises a coupling arrangement, which includes an emitter component and a receiver component that are galvanically separated from each other. The triggering signal from the evaluation circuit can be transmitted via the emitter component to the receiver component that is connected to the switching unit or is associated with the switching unit.

In one exemplary embodiment, the emitter component is the triggering element. In doing so, the receiver component may be connected to a control input of a triggerable semiconductor switch of the switching arrangement.

The emitter component may be, for example, a light-emitting diode, and the receiver component may be at least one photodiode or at least one phototransistor. For example, the emitter component and the receiver component may be arranged as a complete assembly in a shared housing. For example, this assembly may be an optocoupler.

It is advantageous when the receiver component is connected—via a charging and discharging circuit—to the at least one control input of the switching unit. By means of the charging and discharging circuit, it is possible to maintain the first switching state of the switching unit during a dissection request (e.g., actuation of the first switch) even during the period during which a first half-wave is pending. Preferably, the charging and discharging circuit is also adapted to decrease the electrical charges in the at least one control input of the switching unit if no voltage suitable for dissection is to be applied to the cutting electrode, in order to allow a switching of the switching unit into the second switching state.

In an exemplary embodiment, the switching unit may be constructed without mechanical switches and comprise only semiconductor switches such as, for example, bipolar transistors and/or field effect transistors and/or IGBTs.

It is advantageous if the first switch and the triggering element are connected in series in a first evaluation branch. The first evaluation branch can be connected to the evaluation connection. As a result of this, a current flow through the triggering element can be prevented when the first switch is open.

For example, a one-way current path may exist in the first evaluation branch, in which the triggering element is arranged. In the one-way current path, the current flow is allowed only in one direction, in particular in the direction of flow of the current when the second half-wave of the evaluation signal is present. To do so, the one-way current path contains at least one component that has a diode function. The component with the diode function may be the triggering element itself, for example. Alternatively or additionally, an additional component having a diode function—in the simplest case a diode—may be provided in the one-way current path. As an alternative to the diode, it is also possible to use controlled semiconductor switches that assume their conductive state only during a second half-wave of the evaluation signal.

In one exemplary embodiment, the triggering element is configured as a light-emitting diode. In addition to the light-emitting diode in the one-way current path, a separate diode can be connected in series with the triggering element, preferably upstream in the direction of the current flow.

Furthermore, it is advantageous if an additional parallel current path is present in the first evaluation branch parallel to the one-way current path, in which a resistor may be provided, for example. When reference is made to a resistor in the present application, this is meant to be an Ohmic resistor, unless stated otherwise. Preferably, the first switch is connected in series with the one-way current path and the parallel current path.

In one embodiment of the invention, the evaluation circuit includes a manually actuatable second switch. The two switches may be configured in such a manner that they can be actuated independently of each other, i.e., respectively individually or also both at the same time. Alternatively, the two switches may also be mechanically coupled so that, at all times, only one of the two switches can be actuated—as it is the case, for example, with a rocker switch. In a preferred exemplary embodiment, the first switch and the second switch each are configured as push buttons, which are in a blocking state in idle mode and can be manually switched into the conductive state.

It is additionally advantageous if the second switch is arranged in a second evaluation branch of the evaluation circuit. The second evaluation branch is connected to the evaluation connection. Preferably, a resistor is connected in series to the second switch.

In one exemplary embodiment, the second switch and the triggering element are coupled via a connecting current path. For example, the connecting current path may establish a permanent, non-interruptible electrical connection between the two switches and the triggering element. The connecting current path may be configured so as to be free of components. In particular, the second switch and the connecting current path are switched parallel to the triggering element and the first switch. When the second switch is closed or conductive, a low-resistance bridging of the triggering element is established. When the second switch is conductive, it is thus not possible for current to flow through the triggering element. A low-resistance bridging of the triggering element means a bridging that has such a low resistance value that the voltage decrease at the bridging is essentially equal to zero and, in particular, lower than an activating voltage of the triggering element, for example the forward voltage of a light-emitting diode.

It is additionally advantageous if the first coagulation output of the operating circuit is connected to the supply input without a switch. For example, a capacitor may be arranged in this connection.

Preferably the operating circuit comprises a transformer circuit with a transformer. The transformer circuit is connected to the supply input on the primary side and to the cutting output on the secondary side, wherein these connections may be direct or indirect. The transformer of the transformer circuit may be embodied without galvanic separation as an autotransformer. Alternatively, the transformer may also have a primary side that is galvanically separated from the secondary side. In particular, the transformer circuit is adapted to increase the supply voltage applied to the supply connection from, for example, approximately 100 Volt to approximately 450 Volt ac voltage.

A method for operating an instrument for the coagulation and dissection of biological tissue, in particular with the use of the instrument described hereinabove comprises the following steps:

First, an evaluation signal having first half-waves with one polarity and second half-waves with the respective other polarity is applied to the evaluation connection. Subsequently, it is evaluated whether the first switch is in its conductive state or in its blocking state. This evaluation is carried out during at least one of the first half-waves. During at least one of the following second half-waves, a triggering signal is generated for the switching unit, depending on the evaluation result. In particular, if it has been determined that the first switch was manually actuated, a supply voltage is then applied to the supply input. The instrument generates a triggering signal that switches the switching unit—with the first switch actuated—into the first switching state, in which the cutting output—preferably via a transformer circuit—is connected to the supply connection, so that an electrical voltage or an electrical current is made available at the cutting outlet that is suitable for dissection.

In particular, a voltage suitable for dissection or a current suitable for dissection is not applied to the cutting electrode when it was determined that the second switch of the instrument was actuated, independently of the actuation state of the first switch. In this case, a triggering signal is generated that switches the switching unit into the second switching state.

BRIEF DESCRIPTION OF THE DRAWINGS

Advantageous embodiments of the invention can be inferred from the dependent patent claims, the description and the drawings. Hereinafter, preferred exemplary embodiments of the invention will be explained in detail with reference to the appended drawings. They show in FIG. 1 a schematic representation of a device 20 for coagulation and dissection with an apparatus and an instrument that is electrically connected to the apparatus, FIG. 2 a perspective partial representation of a tool of the instrument as in FIG. 1, FIG. 3 a circuit diagram of an exemplary embodiment of an operating circuit of the instrument, FIG. 4 a schematic representation of a chronological behavior of an exemplary triggering signal, FIGS. 5-12 a circuit diagram of an exemplary embodiment of an evaluation circuit of the operating circuit as in FIG. 3, in different states, respectively, FIG. 13 a circuit diagram of an optional voltage increasing circuit for the operating circuit as in FIG. 3, FIG. 14 a modified exemplary embodiment for the implementation of a diode function by means of a transistor, and FIG. 15 a circuit diagram for a modified exemplary embodiment for a switching unit for the operating circuit as in FIG. 3.

DETAILED DESCRIPTION

Figure 1:
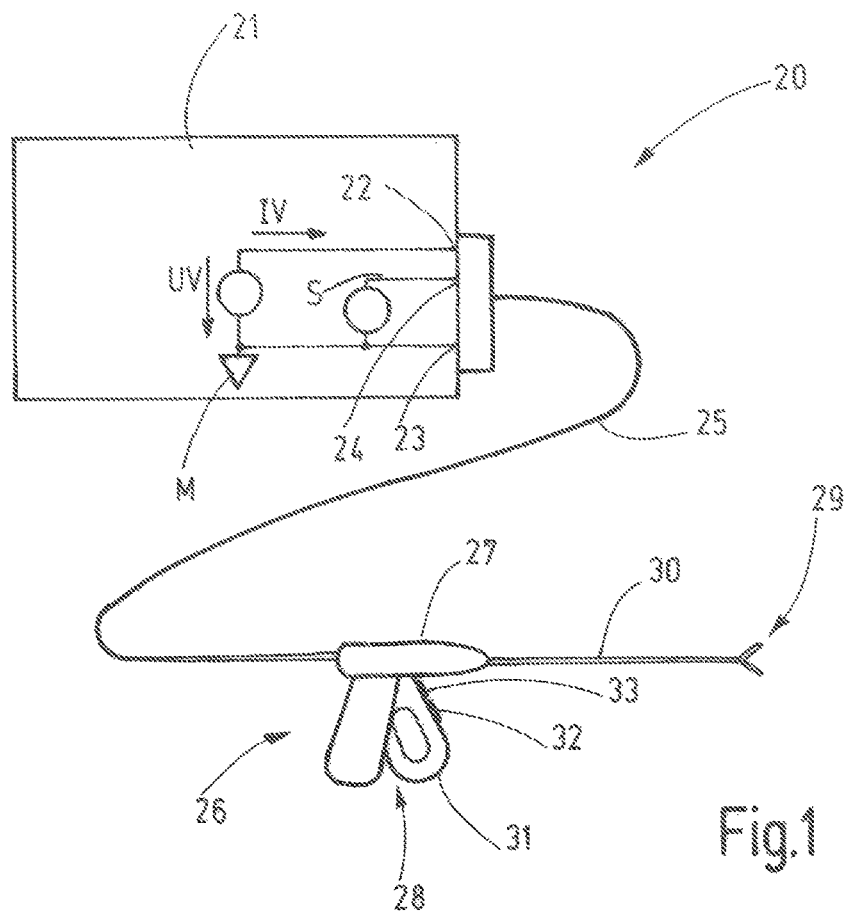
Figure 4:
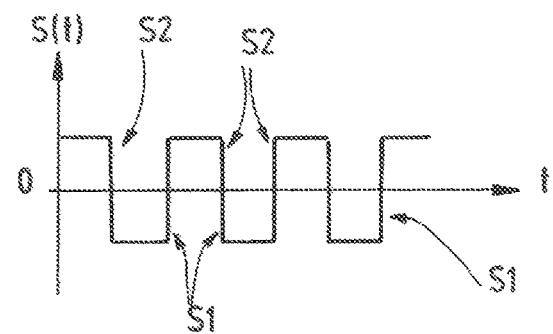

FIG. 1 illustrates a device 20 for coagulation and dissection. The device 20 comprises an apparatus 21 that provides, on a first apparatus output 22, a supply voltage UV or a supply current IV. A second apparatus output 23 is connected to ground M. An evaluation signal S is provided at a third apparatus output 24. In the exemplary embodiment, the evaluation signal S is a periodic signal, for example a voltage or a current, with first half-waves S1 having one polarity and second half-waves S2 having respectively the other polarity. In the exemplary embodiment, the first half-waves S1 are negative and the second half-waves S2 are positive, as is schematically depicted in FIG. 4. In FIG. 4, the evaluation signal S is shown as a rectangular signal. As an alternative, the evaluation signal S could also display any other waveforms, for example a sinusoidal or triangular waveform, with positive and negative half-waves.

Preferably, the evaluation signal S is periodic. In modification of the illustrated exemplary embodiment, it is however also possible for the evaluation signal S to be aperiodic. Furthermore, it is possible for the period of a first half-wave and the period of a second half-wave to have different lengths. In FIG. 4, the first half-waves S1, as well as the second half-waves S2, have the same chronological length, so that each half-wave S1, S2 corresponds to the duration of half a period.

An instrument 26 for coagulation and dissection is connected to the apparatus 21 via a multicore cable 25. The instrument 26 comprises a housing 27 with a handle 28, as well as a tool 29. In the exemplary embodiment, the tool 29 is connected to the housing 27 via connecting part 30. The connecting part 30 may have the shape of a rod. A control element 31 for the tool 29 is provided on the handle 28. The control element 31 is adapted for the mechanical and electrical actuation of the tool 29. A manually actuatable first switch 32, as well as a manually actuatable second switch 33 are provided on the control part 28. In the exemplary embodiment, the two switches 32, 33 are configured as push buttons and are in an electrically blocking state in their not actuated idle mode.

Figure 2:
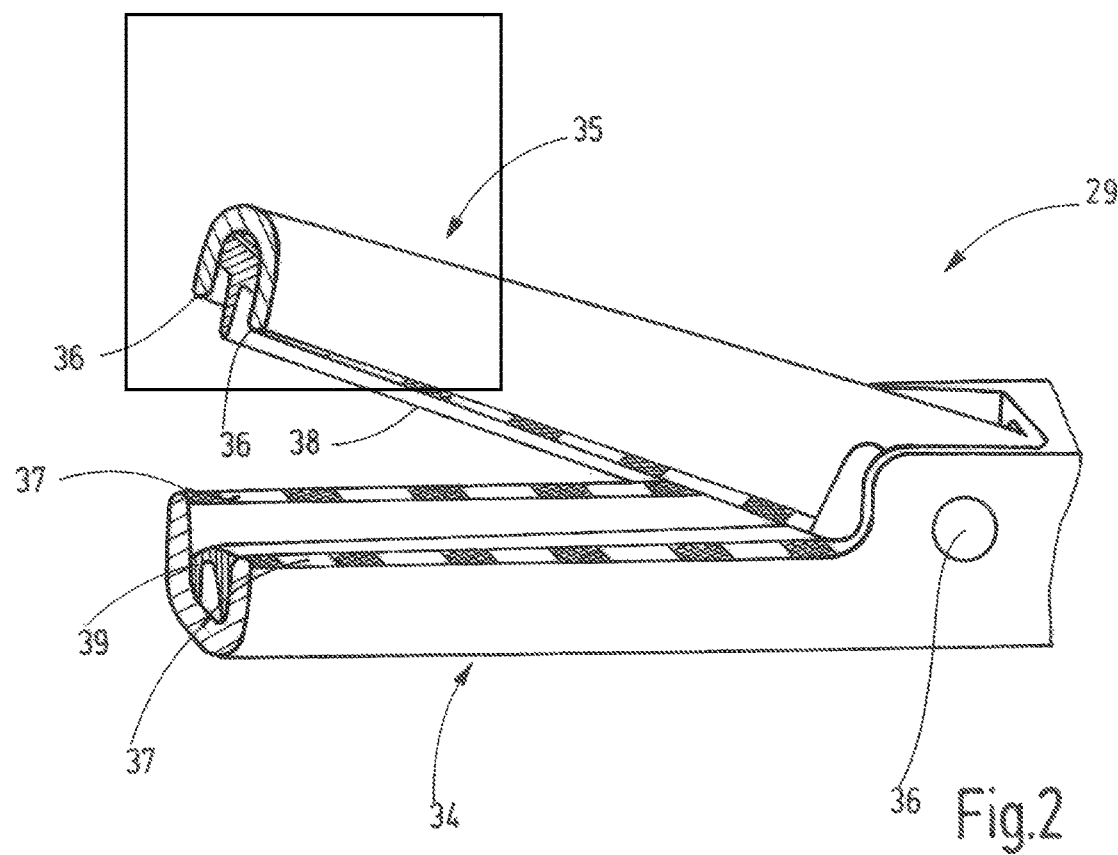

FIG. 2 shows the tool 29 of the instrument 26 of FIG. 1, in a perspective partial representation. The tool 29 has two branches 34, 35 which can be moved relative to each other, said branches being linked to each other in a joint 36. The branches can be moved relative to each over via the control element 31. At least one coagulation electrode 36 is arranged on the one branch, while at least a second coagulation electrode 37 is provided on respectively the other branches. One coagulation electrode 36 and one associate second coagulation electrode 37 form a coagulation electrode pair. Several coagulation electrode pairs may be present on the branches 34, 35.

Furthermore, one of the branches additionally possesses a cutting electrode 38. In the exemplary embodiment, the cutting electrode 38 is arranged as an insert in a groove-shaped recess on the branch 35 and flanked by two first coagulation electrodes 36. The cutting electrode 38 is arranged on the tool so as to be electrically insulated from the first coagulation electrodes 36. The several first coagulation electrodes 36 may be electrically connected to one another.

The branch 34 is associated with a counter-bearing 39 for the cutting electrode 38. When the tool 29 is closed via the control element 31, one first coagulation electrode 36 and one second coagulation electrode 37, respectively, are positioned opposite each other. The cutting electrode 38 abuts adjacent to, or against, the counter-bearing 39. The electrical functions of the electrodes 36, 37, 38 can be performed via the switches 32, 33.

Figure 3:
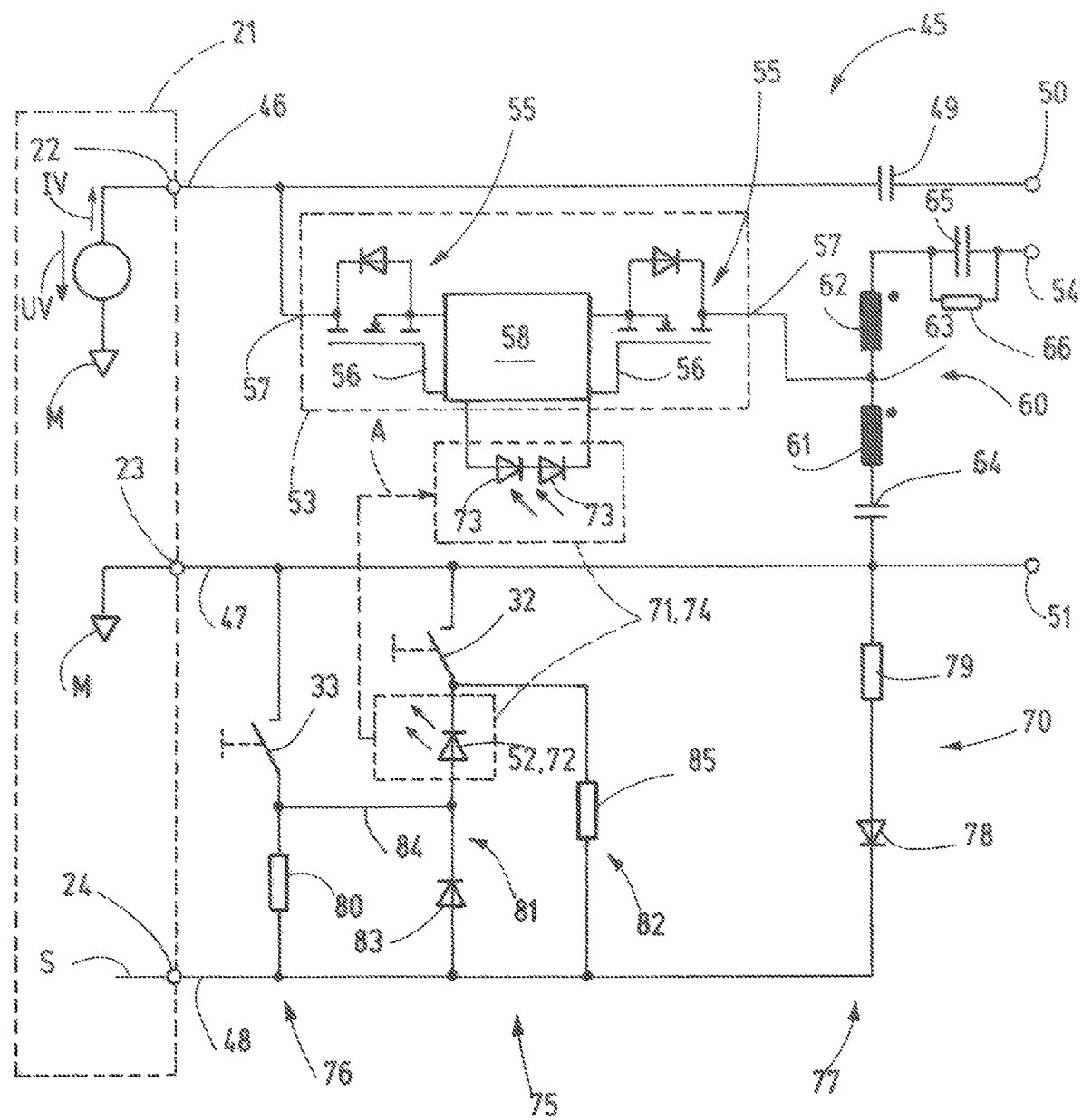

FIG. 3 shows an exemplary embodiment of an operating circuit 45 of the instrument 26. The operating circuit 45 comprises a supply connection 46, by means of which the operating circuit 45 can be connected to the first apparatus output 22, as well as a ground connection 47, by means of which the operating circuit 45 can be connected to the third apparatus output 24. An evaluation connection 48 of the operating circuit 45 can be connected to the third apparatus output 24. Therefore, the evaluation signal S of the apparatus 21 is applied to the evaluation connection 48. The operating circuit 45 is connected to ground M via the ground connection 47. The supply connection 46 is connected to an HF current source or an HF voltage source of the apparatus 21 in order to make available a supply current IV or a supply voltage UF for the operating circuit 45.

The supply connection 46 is connected to a coagulation output 50 via a first capacitor 49. The first coagulation output 50 is connected to the at least one first coagulation electrode 46. A second coagulation output 51 is connected to the at least one second coagulation electrode 47. In the exemplary embodiment, the second coagulation output 51 is configured as the ground output. To do so, the second coagulation output 51 is connected to the ground connection 47 and thus to ground M.

Furthermore, the operating circuit 45 comprises a switching unit 53 that can be switched by means of a triggering signal A of a triggering element 52. The switching unit 53 is switched in the electrical connection between the supply connection 46 and a cutting output 54. The switching unit 53 is adapted to provide—on the cutting output 54 in a first switching state—a voltage and/or a current, which is adapted for a dissection with the use of the cutting electrode 38 and to essentially not provide electrical energy in a second switching state on the cutting output 54. In the second switching state, according to the example, the connection between the supply connection 46 and the cutting output 54 is interrupted.

The switching unit 53 is embodied without mechanical switches and comprises at least one semiconductor switch 55 and, in the exemplary embodiment, two serially connected semiconductor switches 55. In accordance with the example, each semiconductor switch 55 is a field effect transistor that, here, is depicted as a normally blocking N-channel MOSFET. Each semiconductor switch 55 has a control connection 56 which, in the exemplary embodiment, is represented by the gate of the MOSFETs.

Preferably, the two control connections 56 are connected to each other. Furthermore, the two source connections of the MOSFETs may be connected to each other (FIG. 13).

Each of the drain connections of the two MOSFETs forms a switching connection 57 of the switching unit 53. The switching path for the switching unit 53 is formed between the two switching connections 57. One switching connection 57 of the switching unit 53 is connected to the supply connection. The respectively other switching connection 57 is connected to the switching output 54.

In accordance with the example, the switching unit 53 comprises a charging and discharging circuit 58 for the at least one semiconductor switch 55. The charging and discharging circuit 58 is adapted to hold electrical charges on the control connections 56 sufficiently long so as to be able to maintain the first switching state of the switching unit 54 from its first half-wave S1 at least up to the next first half-wave S1, as long as the first switch 32 is actuated. On the other hand, the charging and discharging circuit 58 is adapted to discharge charges on the control connections 56 so that the semiconductor switches 55 are able to also return into their non-conductive state, once the first switch 32 is no longer actuated.

In the exemplary embodiment, the operating circuit 45 comprises a transformer circuit with a transformer 60. The transformer 60 has a primary coil 61 and a secondary coil 62. In the exemplary embodiment, the transformer 60 is configured as an autotransformer. In doing so, the primary coil 61 and the secondary coil 62 are connected in series, and a center tap 63 is connected to the associate switching connection 57 of the switching arrangement 53. Starting from the center tap 63, a series circuit consisting of the primary coil 61 and a second capacitor 64 is connected to ground M. Starting from the center tap 63, a series circuit consisting of the secondary coil 62 and a third capacitor 65 is connected to the cutting output 54. A first resistor 66 is connected parallel to the third capacitor 65. The parallel circuit consisting of the third capacitor 65 and the first resistor 66 forms a circuit for early spark detection. If sparks occur, the supply current IV or the supply voltage UV has an equal offset which can be evaluated and detected in the apparatus 21. If such a spark detection is not desired, the circuit for early spark detection may also be omitted.

In addition, the operating circuit 45 comprises an evaluation circuit 70 which is associated with the triggering element 52. The evaluation circuit 70 is coupled with the switching unit 53 via a coupling arrangement 71 in order to transmit the triggering signal A from the evaluation circuit 70 to the switching unit 53. For this purpose, the coupling arrangement 71 has at least one emitter component 72 in the evaluation circuit 70 and at least one receiver component 73 that is connected to the at least one control connection 56 of the switching unit 53. In the exemplary embodiment, the at least one emitter component 72 is a light-emitting diode, and the at least one receiver component 73 is a photodiode or, alternatively a phototransistor. Thus, the coupling arrangement 71 may be an optocoupler 74. In the exemplary embodiment shown here, the emitter component 72 is a triggering element 52.

In the exemplary embodiment depicted by FIG. 3, the evaluation circuit 70 comprises a first evaluation branch 75 with the first switch 32, a second evaluation branch 76 with the second switch 33, as well as a third evaluation branch 77. The three evaluation branches 75, 76, 77 are connected in parallel to each other between the ground connection 47 and the evaluation connection 48.

In the exemplary embodiment, the third evaluation branch 77 is represented by a series circuit comprising a first diode 78 and a second resistor 79. The cathode of the first diode 78 is connected to the evaluation connection 58 and the anode of the second resistor 79. The other connection of the second resistor 79 is connected to ground M.

The second evaluation branch 76 comprises—in addition to the second switch 33—a third resistor 80 that is connected in series with the second switch 33.

The first evaluation path 75 has a one-way current path 81 connected in series to the first switch 72, as well as a parallel current path 82 connected parallel to the one-way current path. In the one-way current path 81, the triggering element 52 is connected in series to the first switch 32. The one-way current path 81 comprises at least one component having a diode function, so that a current can flow in the one-way current path 81 only in one direction and, as in the example, from the evaluation connection 48 to the ground connection 47, as long as the first switch 32 is closed. In the exemplary embodiment depicted here, an additional component having a diode function, according to the example a second diode 83, is connected in series to the triggering element 52. The anode of the second diode 83 is connected to the evaluation connection 48, and the cathode of the second diode 83 is connected to the triggering element 52 and, as in the example, to the anode of the light-emitting diode forming the triggering element 52.

Furthermore, the connecting point between the second diode 83 and the triggering element 52 in the illustrated exemplary embodiment is connected—via a connecting current path 84—to the second switch 33, so that the connecting current path 84 and the second switch 33 are connected parallel to the triggering element 52 and the first switch 32.

In the parallel current path 82, parallel to the second diode 83 and the triggering element 72, there is connected a fourth resistor 85.

The operation of the operating circuit 45 is described hereinafter with reference to FIGS. 5 to 12. In order to make a distinction, a current flowing through the first evaluation branch 75 is referred to as the first current I1, a current flowing through the second evaluation branch 76 is referred to as the second current I2, and a current flowing through the third evaluation branch 77 is referred to as the third current I3. The resistance values of the resistors 79, 85 and 80 in the evaluation circuits 75, 76, 77 are selected such that the apparatus 21 detects, based on the intensity of the currents I1, I2, I3 whether or not a switch 32, 33 is in its conductive state. In particular the resistance values of the third resistor 80 and the fourth resistor 85 are different. As a result of this, it is possible to detect in the apparatus 21 which of the switches 32, 33 is conductive during a first half-wave S1 and which of the switches 32, 33 is blocking, respectively.

Figure 5:
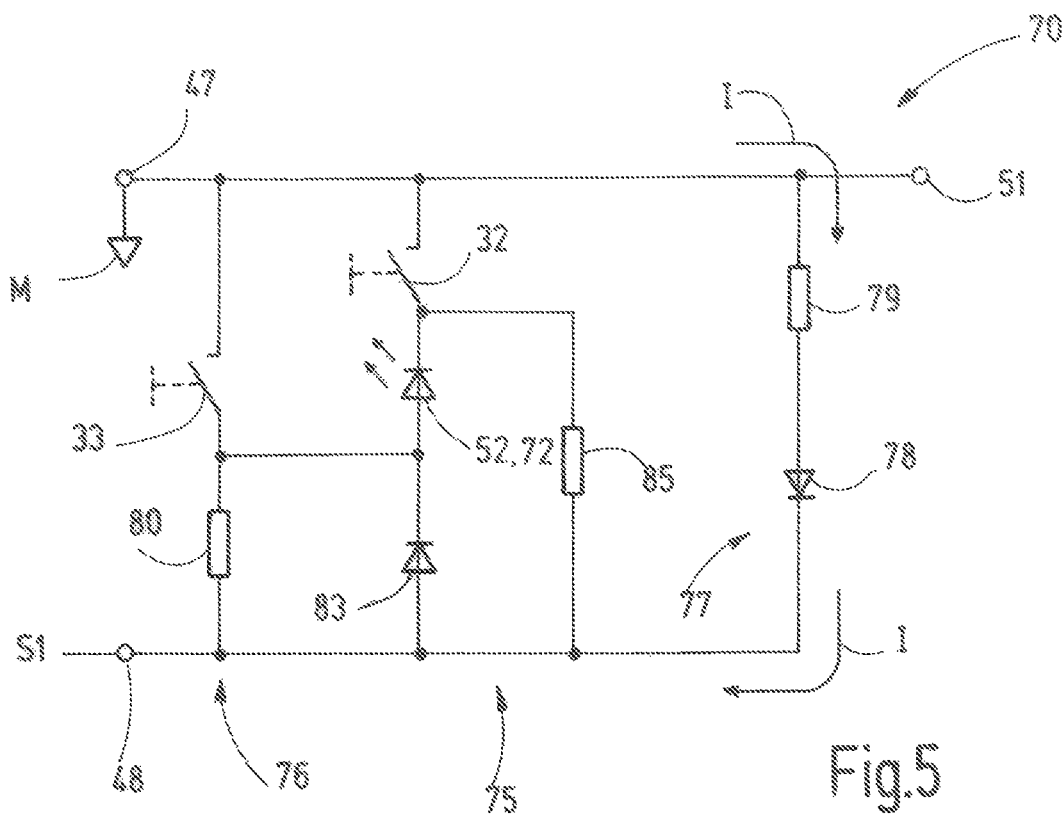
Figure 6:
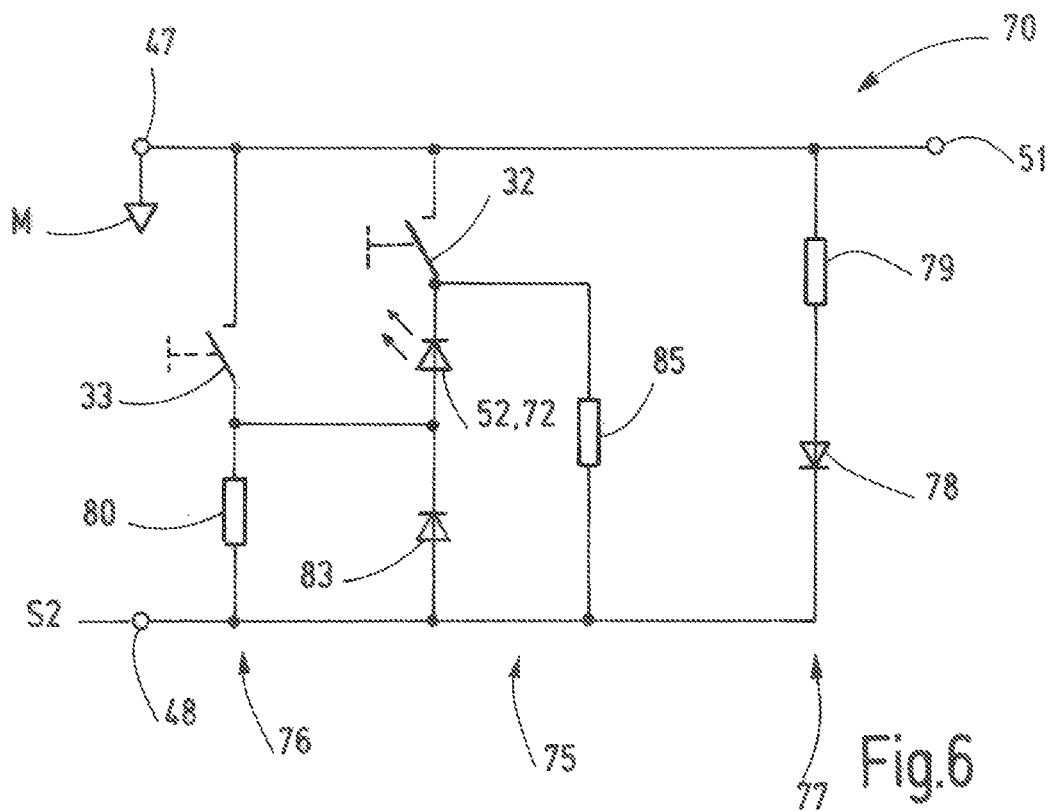

It is assumed that both switches 32, 33 of the evaluation circuit 70 (e.g., in their respective initial state) are not conductive, as is illustrated by FIGS. 5 and 6. During the first half-waves S1 of the evaluation signal S, a third current I3 flows only through the third evaluation path 77 and consequently through the second resistor 79 and the first diode 78 (FIG. 5). The apparatus 21 is able to detect—by evaluating the third current I3—that the other two evaluation paths 75, 76 are interrupted and that, consequently, neither a coagulation nor a cutting operation are to be performed. During the second half-waves S2, no current flows though the evaluation circuit 70 (FIG. 6).

Figure 7:
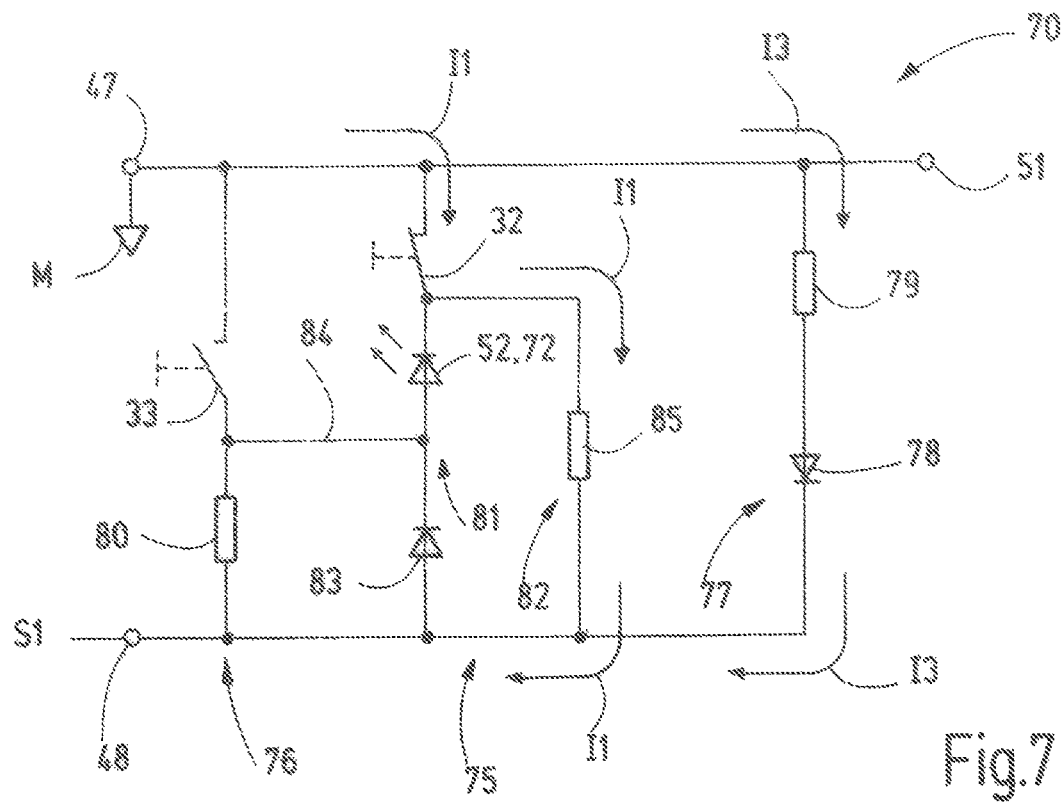
Figure 8:
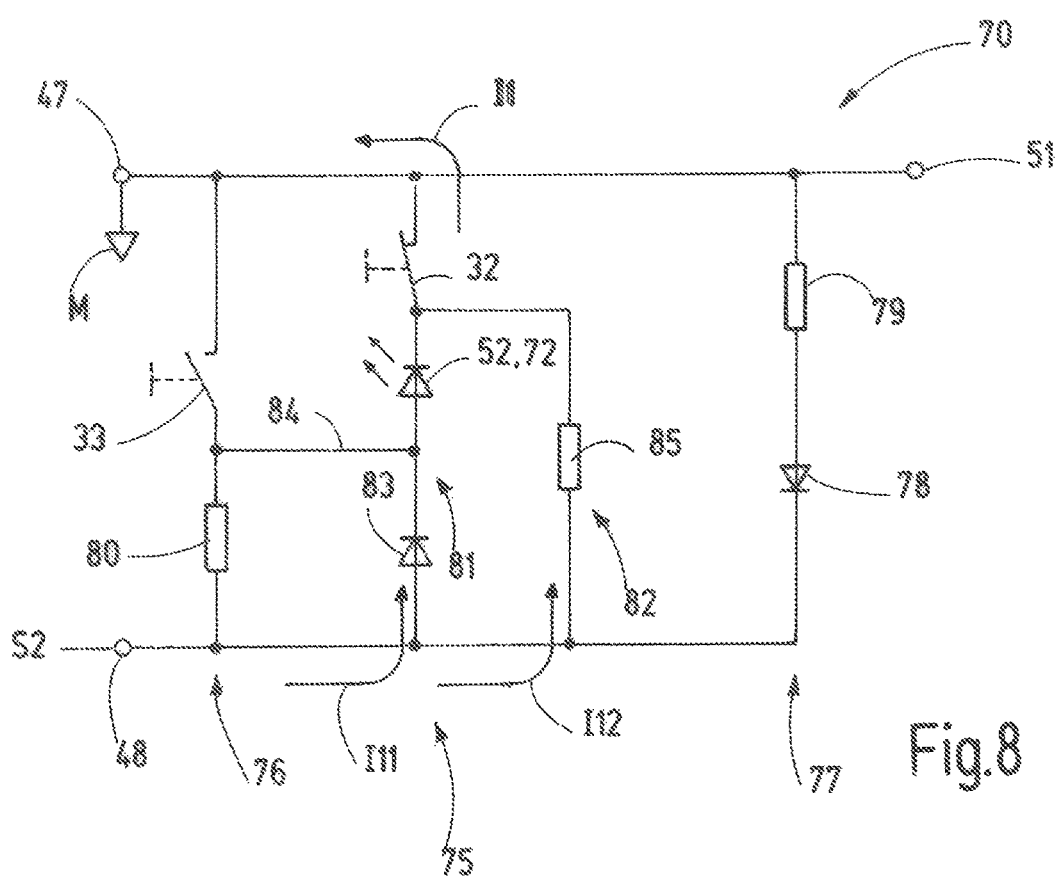

Now it is assumed that a user of the instrument actuates the first switch 32 so that said switch is switched into its conductive state, as illustrated by FIGS. 7 and 8. During the first half-wave S1, a first current I1 flows through the first evaluation branch 75, and a third current I3 flows through the evaluation branch 77 (FIG. 7). In doing so, the first current I1 flows through the first switch 33 and in the parallel current path 82, i.e., through the fourth resistor 85. During one or more first half-waves S1, the apparatus 21 can therefore detect that the first switch 32 was actuated and is in its conductive state, while the second switch 33 is not conductive.

After it was detected that the first switch 32 was actuated, the supply voltage UV and the supply current IV, respectively, are made available at the first apparatus output 22 and thus at the supply connection 46.

During a subsequent second half-wave S2 (positive half-wave), no current will flow during the third evaluation branch 77 due to the first diode 78. The first current I1 through the first evaluation branch 75 has a partial current I11 through the one-way current path 81 and a partial current I12 through the parallel current path 82. The partial current I11 in the one-way current path 81 is clearly greater due to the lower resistance value—compared to the fourth resistor 85—than the partial current I12 through the parallel current path 82. The partial current I11 flows through the triggering element 52 that, at the same time, represents the emitter component 72. The triggering signal A is transmitted to at least one receiver component 73 and switches the switching unit 53 into the first switching state. in which the at least one semiconductor switch 55 is conductive and establishes an electrical connection between the switching connections 57. According to the example, the triggering signal A is formed by the light transmitted from the light-emitting diode (emitter component 72) of the optocoupler 74, said light ensuring that, in accordance with the example, two photodiodes of the optocoupler 74 generate a voltage that acts as the source for the generation of a drain-source voltage or the base-emitter voltage through the charging and discharging circuit 58 and thus switches the at least one semiconductor switch 55 into the conductive state.

The at least one receiver component 73 is connected to the control connection 56 of each semiconductor switch 55 via the charging and discharging circuit 58 in order to, on the one hand, be able to hold the charges long enough in the control connections 56 (at least during the period of a first half-wave S1) and, on the other hand, be able to again discharge charges existing there when the switching unit 53 is to be switched to the second switching state.

In the exemplary embodiment, the charge is maintained in the gate connections of the MOSFETs via the charging and discharging circuit 58, so that the switching unit 53 also remains in its second switching state (conductive state) when a first half-wave S1 is pending. At least for the duration of a first half-wave S1, the charge is maintained in the gates of the MOSFETs by the charging and discharging circuit 58, when the photodiodes of the optocoupler 74 are again triggered by the light-emitting diode of the optocoupler 74, while the first switch 32 is conductive and during a second half-wave S2.

Figure 9:
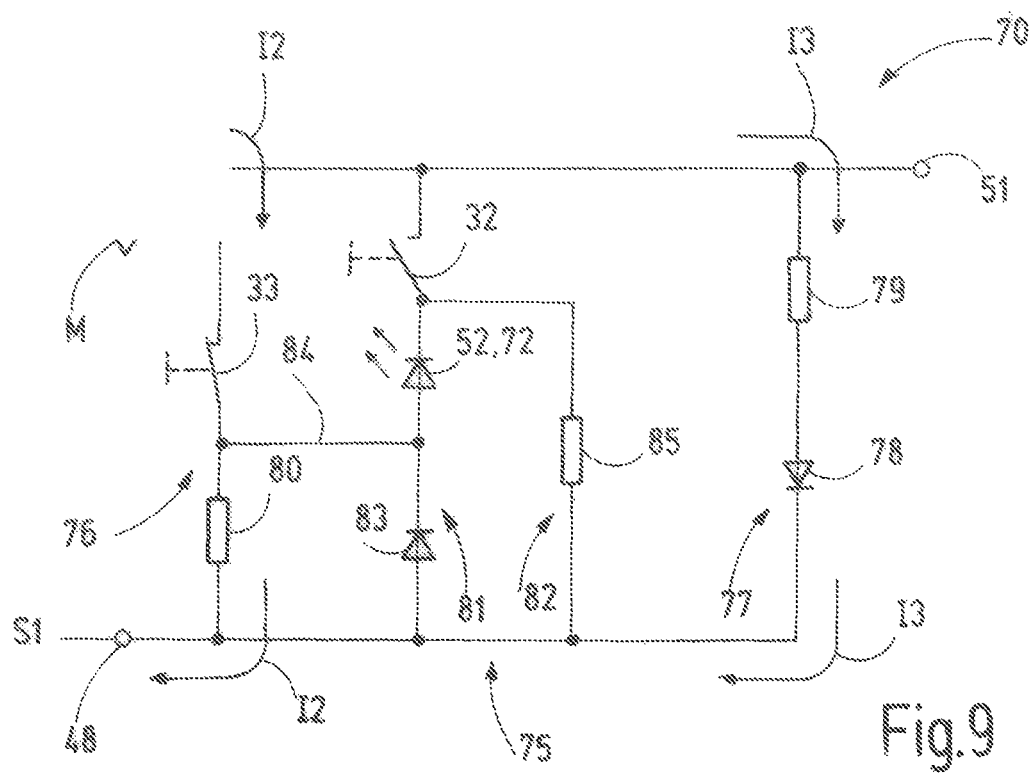
Figure 10:
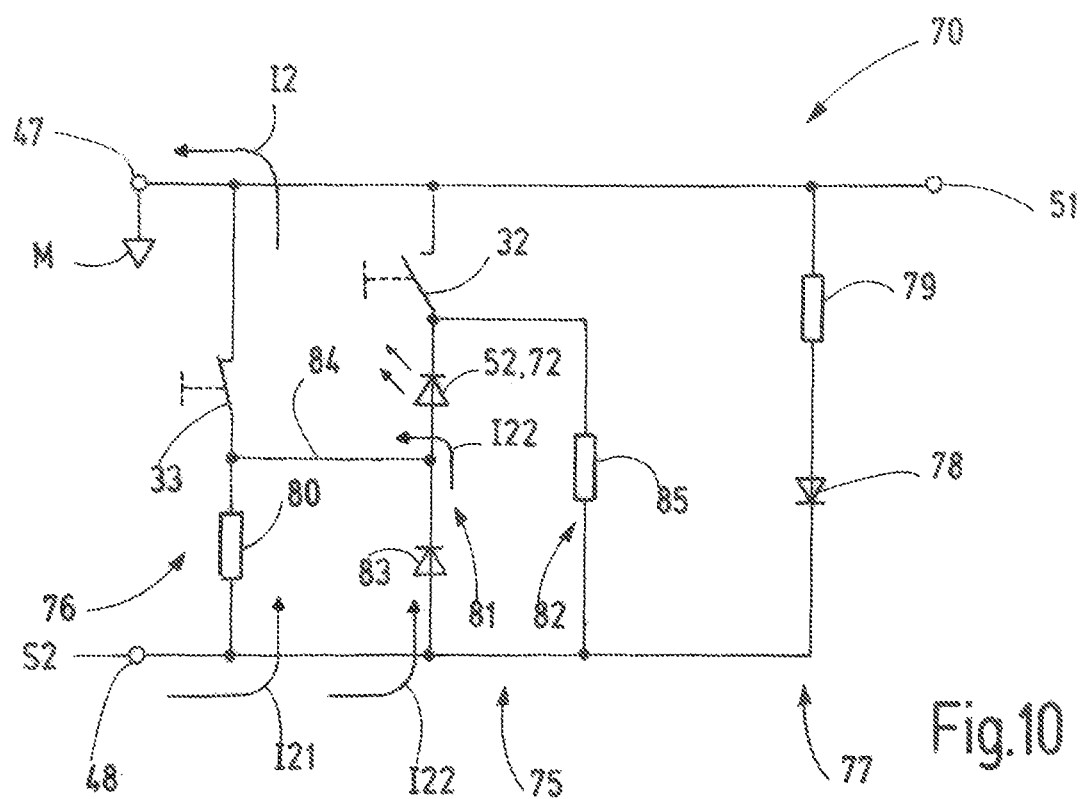

FIGS. 9 and 10 show another state, in which the first switch 32 is not conductive but the second switch 33 was actuated and is thus in its conductive state. During the first half-wave S1 of the evaluation signal S, a second current I2 flows through the second evaluation branch 76, and a third current I3 flows through the second evaluation branch 76, and a third current I3 flows through the third evaluation branch 77 (FIG. 9). The apparatus 21 detects that, in doing so, the currents flow through the second resistor 79 and the third resistor 80 and can thus determine that the second switch 33 is conductive, that, however, the first switch 32 is not conductive and thus cannot be actuated. Subsequently, the apparatus 21 provides the supply voltage UV or the supply current IV to the first apparatus output 22 and thus to the supply connection 46, which voltage is thus available at the first coagulation output 50.

The switching unit 53 remains in its second switching state in that no voltage and no current, respectively, will be made available at the cutting output. This is achieved in that, during the second half-waves S2, a second current I2 flows through the second switch 33, wherein a partial current I21 of the second current I2 flows through the second diode 83 and in the connecting current path 84. In any event, the triggering element 52 or the emitter component 72 are currentless, so that the semiconductor switches 55 remain in their non-conductive state (FIG. 10).

Figure 11:
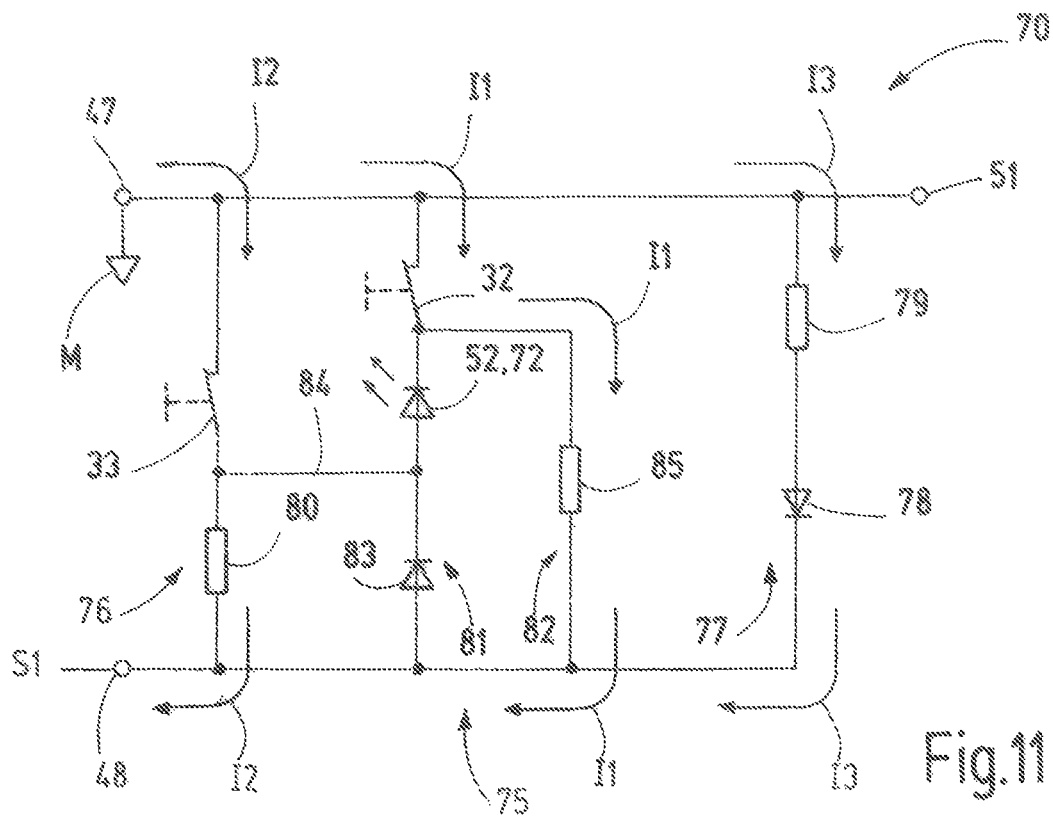
Figure 12:
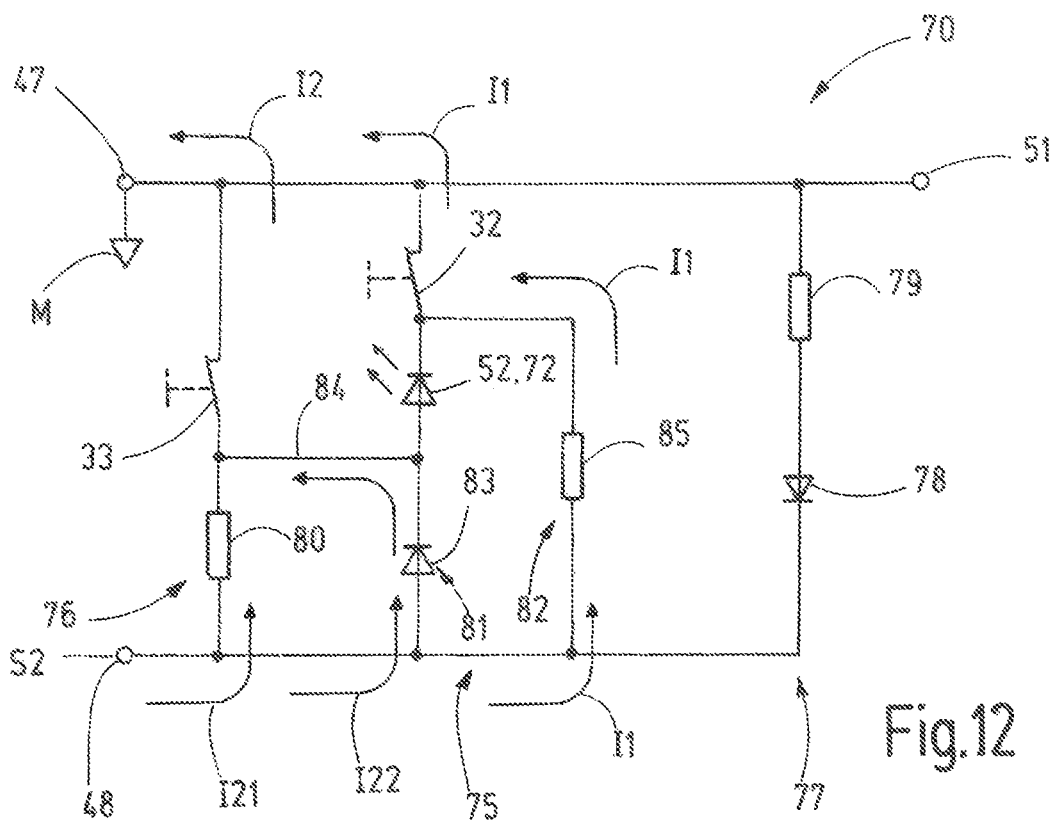

It is now assumed that a user actuates the first switch 32, as well as the second switch 33, and that thus both switches 32, 33 assume their conductive state (FIGS. 11 and 12). During the first half-waves S1 (FIG. 11) a first current I1 flows through the first evaluation branch 75, wherein the first current I1 flows through the first switch 32 and the parallel current branch 82. A second current I2 flows through the second evaluation branch 76, and a third current I3 flows through the third evaluation branch 77. In doing so, it is found that at least one of the switches 32, 33 is actuated, and the apparatus 21 provides a supply voltage UV or a supply current IV to the first apparatus output 22.

During a second half-wave S2 (FIG. 12), a second current I2 flows through the first switch 33 of the second evaluation branch 76, which is composed of a partial current I21 through the resistor 80 and of a partial current I22 through the second diode 83 and the connecting current path 84. A first current I1 flows in the parallel current path 82 and the first switch 32. The triggering element 52 or the emitter element 72 is bridged or short-circuited in a low-resistance manner by the second switch 33. Consequently, it is prevented—without any mechanical means due to the construction of the evaluation circuit 70—that a cutting voltage would be applied to the cutting electrode 30 when the second switch 33 is actuated. Therefore, any inadvertent cutting is not possible when the second switch 33 is actuated in order to prompt a coagulation.

FIG. 13 shows an exemplary embodiment of a charging and discharging circuit 58. It is understood that it is possible to also use other charging and discharging circuits.

The at least one receiver component 73 has a connection 73a displaying higher electrical potential (here: anode side of the at least one photodiode) and a second connection 73b displaying lower electrical potential (here: cathode side of the at least one photodiode). During a triggering by the emitter component 72, a higher potential will be applied to the first connection 73a than to the second connection 73b.

A fifth resistor 90 is connected in parallel to the at least one receiver component 73. An anode of a third diode 91 is connected to the first connection 72, while its cathode is connected to a fourth capacitor 92. The other side of the fourth capacitor 92 is connected to the second connection 73b. The fifth resistor 90 is connected in parallel to the series circuit comprising the third diode 91 and the fourth capacitor 92.

A series circuit comprising a fourth diode 93 and a fifth capacitor 94 is connected parallel to the third diode 91, wherein the anode of the fourth diode 91 is connected to the cathode of the third diode 91. The cathode of the fourth diode 93 is connected to an anode of a fifth diode 95. The cathode of the fifth diode 95 is connected to a sixth capacitor 96. The other connection of the sixth capacitor 96 is connected to the second connection 73b. Furthermore, the sixth capacitor 96 is connected between the control connections 56 (drain connections) and the connecting point between the two series-connected semiconductor switches 55 (source connections). A sixth resistor 97 is connected parallel to the sixth capacitor 96.

The several cascades, each consisting of a diode 91, 93, 95 and a series-connected capacitor 92, 94, 96, are adapted for voltage multiplication of the voltage applied to the at least one receiver component 73 when the emitter component 72 is triggered. Due to the existing capacitors, the triggering of the semiconductor switches 55 and, in accordance with the example, the charge in the gates of the field effect transistors can be maintained, even if—during a first half-wave S1—there is no voltage applied to a first receiver component 73 for a short time. Consequently, the capacitors also act as buffer capacitors. To allow discharging, the resistors 90, 97 of the charging and discharging circuit 58 are provided. After the first switch 32 is deactuated, the charges in the triggering connections 56 can balance via the resistors 90, 97, and the semiconductor switches 55 can return into their blocking state. The period from switching the first switch 32 into the non-conductive state to the blocking of the semiconductor switch 55 depends on the dimensioning of the components present in the charging and discharging circuit 58.

In modification of the charging and discharging circuit 58 described hereinabove, it is also possible to use more or fewer cascades of diodes and capacitors. This depends on the type of voltage needed for the issue through the semiconductor switch 55.

FIG. 14 shows a modified embodiment of the third evaluation branch 77, wherein, instead of the first diode 78, a transistor, in particular a bipolar transistor, is used, the collector connection of said transistor being connected to the second resistor 79 and its emitter connection being connected to the evaluation connection 48. The base connection of the transistor is connected to ground via a seventh resistor 101.

FIG. 15 shows a modified exemplary embodiment of the switching unit 53. The semiconductor switches 55 comprise bipolar transistors 10 and are each triggered by a semiconductor switch 102. The semiconductor control switches 102 are composed of field effect transistors—according to the example, by normally blocking N-channel MOSFETs. The control connections 56 of the semiconductor control switches 102 are connected to the charging and discharging circuit 58. Furthermore, the two collectors of the bipolar transistors 103 are connected to the charging and discharging circuit 58. Each emitter of a bipolar transistor 103 represents a switching connection 57. Furthermore, the collectors of the bipolar transistors 103 are connected to the source connections of the field effect transistors which form the semiconductor control switches 102. The base of each bipolar transistor 103 is connected to the drain connection of a respectively associate field effect transistor. As soon as the gate-source voltage is sufficiently high, the semiconductor control switches 102 become conductive, so that a base current flows out of the PNP bipolar transistors 103 and they move into their conductive state.

The invention relates to an instrument for the selective coagulation and dissection of biological tissue. The instrument comprises a tool 29 with coagulation electrodes 36 and at least one cutting electrode 38. The electrodes 36, 38 are actuated via an operating circuit 45. The operating circuit 45 comprises an evaluation circuit 70, to which an external apparatus 21 delivers an evaluation signal S with first half-waves S1 and second half-waves S2. The first half-waves S1 and the second half-waves S2 display opposite polarities. During at least one first half-wave S1, the evaluation circuit 70 checks whether a first switch 32 or a second switch 33 or both switches 32, 33 are actuated on the instrument 26. Depending on the evaluation result, a triggering signal A is generated and transmitted to a switching unit 53, in particular with the use of a coupling arrangement 71, with galvanic separation. Depending on the triggering signal A, the switching unit 53 is switched into a first switching state or a second switching state. In the second switching state, no voltage suitable for dissection and no current suitable for dissection, respectively, is applied to the cutting electrode 38. In the first switching state, a voltage suitable for dissection or a current suitable for dissection is applied to the cutting electrode 38. The first switching state is preferably brought about via the triggering signal A when the evaluation circuit 70 detects that only the first switch 32 is actuated.

LIST OF REFERENCE SIGNS

20 Device for coagulation and dissection
21 Apparatus
22 First apparatus output
23 Second apparatus output
24 Third apparatus output
25 Cable
26 Instrument
27 Housing
28 Handle
29 Tool
30 Connecting part
31 Control element
32 First switch
33 Second switch
34 Branch
35 Branch
36 First coagulation electrode
37 Second coagulation electrode
38 Cutting electrode
45 Operating circuit
46 Supply connection
47 Ground connection
48 Evaluation connection
49 First capacitor
50 First coagulation output
51 Second coagulation output
52 Triggering element 53 Switching unit
54 Cutting output
55 Semiconductor switch
56 Control connection
57 Switching connections
58 Charging and discharging circuit
60 Transformer
61 Primary coil
62 Secondary coil
63 Center tap
64 Second capacitor
65 Third capacitor
66 First resistor
70 Evaluation circuit
71 Coupling arrangement
72 Emitter component
73 Receiver component
73a First connection
73b Second connection
74 Optocoupler
75 First evaluation branch
76 Second evaluation branch
77 Third evaluation branch
78 First diode
79 Second resistor
80 Third resistor
81 One-way current path
82 Parallel current path
83 Second diode
84 Connecting current path
85 Fourth resistor
90 Fifth resistor
91 Third diode
92 Fourth capacitor
93 Fourth diode
94 Fifth capacitor
95 Fifth diode
96 Sixth capacitor
97 Sixth resistor
100 Transistor
101 Seventh resistor
102 Semiconductor control switch
103 Bipolar transistor
A Triggering signal
I Current
I1 First current
I11 Partial current
I12 Partial current
I2 Second current
I21 Partial current
I22 Partial current
I3 Third current
IV Supply current
M Ground
S Evaluation signal
S1 First half-waves
S2 Second half-waves
UV Supply voltage

The invention claimed is:

1. An instrument (26) for the coagulation and dissection of biological tissue, comprising:
a tool (29) including at least one cutting electrode (38) and at least one first coagulation electrode (36) and at least one second coagulation electrode (37), and
an operating circuit (45) comprising:
a cutting output (54) connected to the at least one cutting electrode (38), a first coagulation output (50) connected to the at least one first coagulation electrode (36), and a second coagulation output (51) connected to the at least one second coagulation electrode (37),
a supply input (46), which provides a supply voltage (UV) or a supply current (IV),
an evaluation connection (24), which provides an evaluation signal (S) having first half-waves (S1) of one polarity and second half-waves (S2) of another polarity,
an evaluation circuit (70) connected to the evaluation connection (24), which evaluation circuit comprises a manually actuatable first switch (32) and a triggering element (52) for the generation of a triggering signal (A), wherein the evaluation circuit (70) is configured to evaluate during at least one of the first half-waves (S1) whether the first switch (32) was actuated, and to generate the triggering signal (A) depending on the evaluation during at least one of the second half-waves (S2), and
a switching unit (53) comprising at least one switch, the switching unit (53) configured to be actuated by the triggering signal (A), and which is configured to be switched between a first switching state and a second switching state and which is connected to the supply input (46) and the cutting output (54).

2. The instrument according to claim 1, wherein the operating circuit (45) further comprises a coupling arrangement (71), which comprises at least one emitter component (72) and at least one receiver component (73) that is galvanically separated from the emitter component (72).

3. The instrument according to claim 2, wherein the emitter component (72) is the triggering element (52), and the receiver component (73) is connected with a control input (56) of a triggerable semiconductor switch (55) of the switching unit (53) via a charging and discharging circuit (58).

4. The instrument according to claim 1, wherein the switching unit (53) comprises a plurality of serially connected semiconductor switches (55), wherein control inputs (56) of the plurality of serially connected semiconductor switches are directly connected to one another.

5. The instrument according to claim 1, wherein the first switch (32) and the triggering element (52) are serially connected in a first evaluation branch (75), wherein the first evaluation branch (75) is connected to the evaluation connection (24).

6. The instrument according to claim 5, wherein, in the first evaluation branch (75), there is provided a one-way current path (81) in which the triggering element (52) is arranged, and at least one component with a diode function is provided in the one-way current path (81) that allows a current flow through the one-way current path (81) only when one of the second half-waves (S2) is present at the evaluation connection (24).

7. The instrument according to claim 6, wherein the triggering element (52) is a light-emitting diode and/or a separate diode (83) is connected in series with the triggering element (52) in the one-way current path (81).

8. The instrument according to claim 6, wherein the first evaluation branch (75) comprises a parallel current path (82) parallel to the one-way current path (81), wherein the first switch (32) is connected in series with the one-way current path (81) and with the parallel current path (82).

9. The instrument according to claim 1, wherein the evaluation circuit (70) comprises a manually actuatable second switch (33).

10. The instrument according to claim 9, wherein the second switch (33) is arranged in an evaluation branch (76), wherein the evaluation branch (76) is connected to the evaluation connection (24).

11. The instrument according to claim 9, wherein, between the second switch (33) and the triggering element (52), there is a connecting current path (84), which, when the second switch (33) is conductive, effects a low-resistance bridging of the triggering element (52).

12. The instrument according to claim 1, wherein the first coagulation output (50) is connected without a switch to the supply input (46).

13. The instrument according to claim 1, wherein the operating circuit (45) further comprises a transformer circuit (60) having primary and secondary sides which is connected to the supply input (46) on its primary side and to the cutting output (54) on its secondary side.

14. A method for operating an instrument (26) for the coagulation and dissection of biological tissue with a tool (29) including at least one cutting electrode (38), at least one first coagulation electrode (36), at least one second coagulation electrode (37), a cutting output (54) connected to the at least one cutting electrode (38), a first coagulation output (51) connected to the at least one first coagulation electrode (36), a second coagulation output (51) connected to the at least one second coagulation electrode (37), a switching unit (53) that is triggered by a triggering signal (A), which switching unit is configured to be switched between a first switching state and a second switching state and is connected to a supply connection (46) and to the cutting output (54), and including a first switch (32) and an evaluation connection (24), the method comprising the following steps:
   applying an evaluation signal (S) with first half-waves (S1) having one polarity and second half-waves (S2) having another polarity to the evaluation connection (24),
   evaluating whether the first switch (32) is in a conductive or blocking state during at least one of the first half-waves (S1),
   generating the triggering signal (A) for the switching unit (53) during at least one of the second half-waves (S2), depending on whether the first switch is in the conductive or blocking state during at least one of the first half-waves (S1).

15. An instrument (26) for the coagulation and dissection of biological tissue, comprising:
   a tool (29) including at least one cutting electrode (38) and at least one first coagulation electrode (36) and at least one second coagulation electrode (37), and
   an operating circuit (45) comprising:
      a cutting output (54) connected to the at least one cutting electrode (38), a first coagulation output (50) connected to the at least one first coagulation electrode (36), and a second coagulation output (51) connected to the at least one second coagulation electrode (37),
      a supply input (46), which provides a supply voltage (UV) or a supply current (IV),
      an evaluation connection (24), which provides an evaluation signal (S) having first half-waves (S1) of one polarity and second half-waves (S2) of another polarity,
      an evaluation circuit (70) connected to the evaluation connection (24), which evaluation circuit comprises a manually actuatable first switch (32) and a triggering element (52) for the generation of a triggering signal (A), wherein the evaluation circuit (70) is configured to evaluate during at least one of the first half-waves (S1) whether the first switch (32) was actuated, and to generate the triggering signal (A) depending on the evaluation during at least one of the second half-waves (S2), and
      a switching unit (53) comprising at least one switch, the switching unit (53) configured to be actuated by the triggering signal (A), and which is configured to be switched between a first switching state and a second switching state and which is connected to the supply input (46) and the cutting output (54),
   wherein the first switch (32) and the triggering element (52) are serially connected in a first evaluation branch (75), wherein the first evaluation branch (75) is connected to the evaluation connection (24).

16. An instrument (26) for the coagulation and dissection of biological tissue, comprising:
   a tool (29) including at least one cutting electrode (38) and at least one first coagulation electrode (36) and at least one second coagulation electrode (37), and
   an operating circuit (45) comprising:
      a cutting output (54) connected to the at least one cutting electrode (38), a first coagulation output (50) connected to the at least one first coagulation electrode (36), and a second coagulation output (51) connected to the at least one second coagulation electrode (37),
      a supply input (46), which provides a supply voltage (UV) or a supply current (IV),
      an evaluation connection (24), which provides an evaluation signal (S) having first half-waves (S1) of one polarity and second half-waves (S2) of another polarity,
      an evaluation circuit (70) connected to the evaluation connection (24), which evaluation circuit comprises a manually actuatable first switch (32) and a triggering element (52) for the generation of a triggering signal (A), wherein the evaluation circuit (70) is configured to evaluate during at least one of the first half-waves (S1) whether the first switch (32) was actuated, and to generate the triggering signal (A) depending on the evaluation during at least one of the second half-waves (S2), and
      a switching unit (53) comprising at least one switch, the switching unit (53) configured to be actuated by the triggering signal (A), and which is configured to be switched between a first switching state and a second switching state and which is connected to the supply input (46) and the cutting output (54),
   wherein the evaluation circuit (70) comprises a manually actuatable second switch (33) and wherein the manually actuatable second switch (33) is arranged in an evaluation branch (76), wherein the evaluation branch (76) is connected to the evaluation connection (24).

* * * * *